(12) United States Patent
Trahan (10) Patent No.: US 10,730,818 B2
(45) Date of Patent: Aug. 4, 2020

(54) SYSTEM FOR SULFIDE TREATMENT IN OILFIELD SYSTEMS

(71) Applicant: David O. Trahan, Lafayette, LA (US)

(72) Inventor: David O. Trahan, Lafayette, LA (US)

(*) Notice: Subject to any disclaimer, the term of this patent is extended or adjusted under 35 U.S.C. 154(b) by 0 days.

(21) Appl. No.: 16/486,805

(22) PCT Filed: Feb. 20, 2018

(86) PCT No.: PCT/US2018/018782
§ 371 (c)(1),
(2) Date: Aug. 16, 2019

(87) PCT Pub. No.: WO2018/152520
PCT Pub. Date: Aug. 23, 2018

(65) Prior Publication Data
US 2020/0031750 A1 Jan. 30, 2020

Related U.S. Application Data

(60) Provisional application No. 62/460,494, filed on Feb. 17, 2017.

(51) Int. Cl.
*C07C 45/52* (2006.01)
*B01J 19/24* (2006.01)
(Continued)

(52) U.S. Cl.
CPC .......... *C07C 45/52* (2013.01); *B01J 19/2415* (2013.01); *B01J 23/30* (2013.01); *B01J 27/1802* (2013.01);
(Continued)

(58) Field of Classification Search
CPC ...... C07C 45/52; C07C 47/22; B01J 19/2415; B01J 23/30; B01J 27/1802;
(Continued)

(56) References Cited

U.S. PATENT DOCUMENTS

| 1,213,143 A | 1/1917 | Alysworth |
| 1,660,403 A | 2/1928 | Turkington |

(Continued)

FOREIGN PATENT DOCUMENTS

GB 141057 A * 6/1921 ............. C07C 45/52

*Primary Examiner* — Huy Tram Nguyen
(74) *Attorney, Agent, or Firm* — Matthews, Lawson, McCutcheon & Joseph, PLLC (57) ABSTRACT

A process for continuous, on-demand production of dilute acrolein liquid on-site, at or near the point of acrolein injection, by the liquid dehydration of glycerol in an improved tubular reactor where non-aqueous glycerol is combined with a heteropolyacid catalyst, including silicotungstic acid, phosphotungstic acid, or phosphomolybdic acid. The acid catalyst is evenly dissolved and dispersed in the glycerol upstream of the reactor vessel. The reaction is conducted in a tubular reactor which is heated to an elevated reaction temperature. The dilute acrolein produced in the tubular reactor is directed downstream, optionally through a liquid-liquid heat exchanger and then an air-liquid heat exchanger to reduce temperature, and then diluted prior to being injected into sulfide contaminated systems (such as oil & gas water floods, water disposal systems, producing oil wells, and fuel oil storage) via a pressure conduit.

20 Claims, 4 Drawing Sheets

(51) Int. Cl.
B01J 23/30 (2006.01)
B01J 27/18 (2006.01)
C10L 3/10 (2006.01)
C07C 47/22 (2006.01)

(52) U.S. Cl.
CPC ..... *C10L 3/103* (2013.01); *B01J 2219/00076* (2013.01); *B01J 2219/00162* (2013.01); *B01J 2219/2419* (2013.01); *C07C 47/22* (2013.01)

(58) Field of Classification Search
CPC .... B01J 2219/00076; B01J 2219/00162; B01J 2219/2419; B01J 23/002; B01J 23/28; B01J 27/19; B01J 27/188; C10L 3/103; C02F 2101/101; C02F 2101/203; C02F 2103/10; C02F 2103/365; C02F 1/683
USPC ....................................................... 422/198
See application file for complete search history.

(56) References Cited

U.S. PATENT DOCUMENTS

| | | |
|---|---|---|
| 2009/0239995 A1 | 9/2009 | Bub et al. |
| 2010/0085708 A1* | 4/2010 | Martin ............... H05K 7/20927 361/696 |
| 2011/0160491 A1 | 6/2011 | Dubois et al. |
| 2013/0111928 A1 | 5/2013 | Bernert, Sr. |
| 2015/0266756 A1 | 9/2015 | Trahan et al. |
| 2015/0353370 A1* | 12/2015 | Fujita ..................... C01C 1/086 252/372 |

\* cited by examiner

SYSTEM FOR SULFIDE TREATMENT IN OILFIELD SYSTEMS

REFERENCE TO RELATED APPLICATIONS

The present application is a US national stage application claiming priority to and benefit of Patent Cooperation Treaty (PCT) application No. PCT/US18/18782, filed 20 Feb. 2018, that in turn claims priority to and benefit of U.S. Provisional Patent Application No. 62/460,494, filed 17 Feb. 2017 and entitled "Apparatus and Method for Sulfide Treatment in Oilfield Systems." The entire content of the above-referenced Patent Cooperation Treaty (PCT) application No. PCT/US18/18782 is incorporated herein by reference.

FIELD

The present invention relates, generally, to a system for continuous production of dilute acrolein, by using a liquid glycerol feedstock in a thermo-catalytic dehydration of glycerol, and the subsequent injection of the produced diluted acrolein into an oil well production flowline, either at or near the wellhead or along the flowline, or directly downhole via a capillary string, or downhole via the annular space in wells without tubing set packers, or via produced water injection systems and water flowlines or conduits to remove iron sulfide and hydrogen sulfide. The apparatus can be easily transported and located at or near the point of injection of the acrolein (e.g., at the wellsite, injection well, or water pond). The use of glycerol for feedstock eliminates the hazards to workers and removes the danger in transporting liquid acrolein in commerce and for storage of the acrolein at warehouses and treating locations.

BACKGROUND

Iron sulfide (FeS) and hydrogen sulfide ($H_2S$) pose serious operating, system, functional, and safety problems in several operational areas of oil & gas production, including water injection systems, oil well flowline and field process systems, oil and water storage tanks, and gas conditioning systems. $H_2S$ present in the liquid or gas phase of oil well production can cause corrosion failures and toxicity problems, as well as combining with iron to form iron sulfide, which can easily deposit in flowlines, plug equipment, plug downhole pumps, plug filters, plug injection lines and form flow blockages at the formation face and within downhole oil and gas producing reservoirs. Iron sulfide is frequently formed under normal operating conditions in oilfield equipment from the combination of iron with $H_2S$ in produced water.

FeS is a challenging problem in oilfield water systems. Several commercial methods have been available to dissolve FeS, for example, sodium hypochlorite, acids, chelating agents, etc. Each of the above methods have drawbacks. Both iron oxide and sulfur are insoluble in water and can result in formation plugging problems. Many different acids can be used to dissolve FeS, however, reaction of acids with FeS can result in the release of $H_2S$ in the atmosphere and in the injection fluid. $H_2S$ is highly undesirable because of its toxicity and, eventually, can lead to reservoir souring. Furthermore, acids lower the pH which can lead to accelerated corrosion rates in metal pipelines and fluid handling equipment.

There are certain chelating agents that demonstrate some effectiveness in converting FeS into soluble iron but only at low $H_2S$ concentrations (<5 ppm). At higher $H_2S$ concentrations in fluids, chelating agents are impeded from action. In comparison, acrolein acts on $H_2S$ and FeS through a chemical reaction with the sulfide element, producing non-toxic, soluble, low molecular weight product. Acrolein is a non-corrosive liquid and is not an oxidizing chemical. The reaction of acrolein with FeS is irreversible and permanently converts the FeS, present in the fluid produced within the oil well system, into a water-soluble product.

Acrolein (also called 2-propenal or acrylic aldehyde) is the simplest unsaturated aldehyde, having a chemical formula of $C_3H_4O$. Acrolein has a boiling point of 53° C. and a high synthetic and technical potential due to the conjugation of the carbonyl group with a vinyl group. Acrolein is a highly toxic material having a distinctive pungent odor, and a flammable material with high environmental polluting potential. Acrolein has enormous industrial applications as a significant intermediate for acrylic acid production. The largest commercial use of acrolein is an intermediate in the synthesis of acrylic acid and as a biocide. Acrolein is currently produced commercially in large quantity by the oxidation of propylene using multi-component mixed oxide catalysts. The primary source of propylene is crude oil.

The production of acrolein from glycerol has been generally known since around 1918. During the early chemical industry days, the limited availability of glycerol or the increased cost of glycerol over the cost of propylene resulted in propylene, which is produced from crude oil, serving as the primary feedstock in the chemical industry.

Acrolein is used successfully in oilfield applications both onshore and offshore for reducing the harmful effects of $H_2S$ and FeS in produced water. Acrolein treatments are very effective in both cost and performance. Several published industry papers describe how effective acrolein is in treatment of $H_2S$ and iron sulfide in oilfield applications: Kissel, Charles L. et al. (1985). SPE 11179, "Factors Contributing to the Ability of Acrolein to Scavenge Corrosive Hydrogen Sulfide." Salma, T. et al. (2000). SPE 59708, "Cost Effective Removal of Iron Sulfide and Hydrogen Sulfide from Water using Acrolein." Penkala, J. E. et al. (2006). SPE 98067 "Acrolein Application to Mitigate Biogenic Sulfides and Remediate Injection-Well Damage in Gas-Plant Water-Disposal System." Horaska, D. D. et al. (2009) SPE 120238, "Field Experiences Detailing Acrolein (2-propenal) Treatment of a Produced Water Injection System in the Sultanate of Oman."

In addition to its ability to dissolve FeS and scavenger $H_2S$, acrolein is also a highly effective micro-biocide used commercially since about 1960 and has found wide use in oil and gas production industry. Acrolein is delivered as a liquid product typically supplied in a regulated, specialized metal container with a special control apparatus to prevent the release from transfers between tanks and injection equipment. Acrolein is difficult to handle and apply due to the toxicity it poses to its handlers and the surrounding workers.

Handling acrolein liquid can present special challenges and requirements to protect workers and the environment. Acrolein is generally delivered to the field location in a pressure tank and discharged using an inert gas. The acrolein containers are built to comply with international transportation regulations for this purpose. The activity of acrolein in treatment water is managed at a dilute concentration in water (below 2%) to safely handle the treatment and to prevent potential polymerization of the acrolein with hydrocarbons. Several handling methods of use have been plagued by the very real possibility of the rupture or leakage of the storage and feeding equipment employed, with consequent probability of toxicity to personnel or animals and/or fire-explosion damage to plants and equipment. Even if the fatal consequences of inhalation, fire or explosion are avoided, the irritation and lachrymation caused by even minute quantities of escaped vapors is a pronounced disadvantage.

Despite the many dangers of using acrolein, it provides a unique all-in-one chemical solution to assist in resolving problems associated with sulfide contamination. Acrolein is highly efficient in scavenging $H_2S$. As a sulfide scavenger, acrolein reacts in a 2:1 molar ratio to form water soluble, irreversible sulfide containing reaction products. The reaction with $H_2S$ is rapid, whereas the reaction with FeS is slower due to the dependence on the shift from FeS to $H_2S$ and soluble iron, whereby it scavenges the $H_2S$. Acrolein can be used for downhole treatment of production and injection wells to control FeS solids, $H_2S$, bacteria, pump failures, and microbiological influenced corrosion (MIC). Acrolein can be useful in the treatment of oil storage tanks, settling tanks, heater treaters and free water knockouts to improve oil water separation and control bacteria. Acrolein can treat water storage air flotation units, water storage tanks, and surge tanks to control sulfide solids and bacteria. Acrolein can treat filters to control bacteria, FeS solids and improve filter run times. Acrolein can protect flow lines and water injection lines by controlling bacteria, FeS solids, MIC, $H_2S$ and under-deposit corrosion. The fact that acrolein is non-corrosive and non-surfactant in nature makes it compatible with surface and downhole equipment and oil-water separation equipment. In addition to oilfield applications of acrolein, it is used as a highly effective aquatic herbicide to control subaquatic plants in water distribution channels, and it is also used as a replacement for pest control agents used for the control of nematode infestation in agriculture.

Glycerol serves as a feedstock to produce acrolein. It is well known in the art to prepare acrolein by dehydrating glycerol. The production of acrolein in the presence of a solid catalyst, also called heterogenous catalyst, has been known for many years. The dehydration of glycerol to produce acrolein, using heterogenous catalysts in continuous flow fixed bed reactors is reported in several industry journals. For example, Herbert in U.S. Pat. No. 2,042,224 teaches the use of a novel process wherein acrolein can be prepared by thermal decomposition of anhydrous glycerol in the presence of certain strong dehydrating agents, such as alkali-metal acid sulfates, phosphorous pentoxide and the like. Howard in U.S. Pat. No. 2,558,520 teaches the use of a method for the preparation of acrolein by the dehydration of glycerol with a dehydration catalyst orthophosphoric acid, metaphosphoric acid or phosphorous pentoxide. Kissel in U.S. Pat. No. 5,081,314 teaches how dilute solutions of acrolein are produced on site and on demand by oxidizing propylene in a reactor using heterogeneous catalysts, which are mixtures of molybdenum, bismuth and tellurium oxides and which are deposited on a metal and used in a packed catalyst bed.

The hazards of handling, shipping, and storing concentrated acrolein can be reduced by diluting it with a solvent, like water. However, storage of dilute acrolein usually results in degradation of the material over time. Water hydrolyzes acrolein, producing hydrolysis products that retain little or no functionality as a sulfide scavenger or iron sulfide dissolver. Maximum levels of acrolein dissolved in water are about 19-25% depending on temperature. After a few days, these levels are reduced to only a few percent. It is generally known that a lower pH extends the life of acrolein in water. Even with the use of acid, after a few months, the acrolein concentration lowers to ineffective concentration levels.

There exists a need for a portable, self-contained system for generating a dilute solution of acrolein in sufficient quantities to satisfy on-demand and on-site requirements, while avoiding the problems arising from safety concerns and the handling of concentrated acrolein.

There exists a need for a system which avoids the use of solid, heterogenous catalyst or a packed catalyst bed, thus reducing the need to regenerate solid catalyst to remove fouling carbon deposits from the surface of solid catalyst. The deactivation, carbonization or coking, remains the main obstacle in the way of transportable and large-scale industrial applications.

There exists a need for a system which utilizes a renewable glycerol feedstock in the production method. Worldwide glycerol production is increasing due to the expansion of bio-diesel production, based upon triglycerides, and has led to a large surplus of its major byproduct glycerol. Glycerol is also produced as a by-product of betaine production, such as cocoamidopropyl betaine, a surfactant used in industrial cleaners and personal care products.

There exists a need for a system whereby the dehydration of glycerol into acrolein occurs within the liquid phase, and not in the vapor phase. The typical vapor phase dehydration of glycerol requires the use of a water-glycol mixture that must be elevated to a high temperature to form a water vapor along glycerol vapor stream at elevated pressures flowing over a heterogenous, solid acid catalyst bed. The solid acid catalysts are often highly prone to carbonization (carbon fouling) leading to greatly reduced reaction efficiencies due to the blockage of active catalyst reaction sites.

There exists a need for a system whereby acrolein may be added to water systems and dispersed without the danger of the entrainment of air within acrolein storage and feeding systems, and the fire and explosive hazards which would otherwise result.

The present invention meets these needs.

SUMMARY OF THE INVENTION

The present application is directed towards an inventive system for producing dilute acrolein solutions with a glycerol feedstock.

In an embodiment, the invention comprises a system of continuous production and injection of acrolein comprising a feedstock container with a mixture of non-aqueous glycerol and at least one heteropolyacid catalyst, a fluid pressure pump carrying the mixture from the feedstock container through a conduit, a tubular reaction chamber in liquid communication with the conduit, wherein the tubular reaction chamber is heated to bring the mixture to a temperature sufficient to activate the at least one heteropolyacid catalyst, wherein the at least one heteropolyacid catalyst dehydrates the glycerol into acrolein. The mixture may enter a liquid-liquid heat exchanger between the feedstock container and the tubular reaction chamber. The system may further comprise a vessel containing a heat transfer liquid and comprising an electric resistance heater, a steam coil, or combinations thereof immersed in the heat transfer liquid, and wherein the heat transfer liquid is heated to room temperature. The tubular reaction chamber may further comprise a coiled conduit of sufficient capacity to hold the mixture within the tubular reaction chamber until the dehydration is completed, or for at least 20 minutes. The temperature of the reaction chamber may be maintained between 260° C. and 300° C. and between 15 and 200 psi. The reaction chamber may be heated by electrical resistance heat, indirect gaseous fuel heat, or an organic heat transfer liquid. The supply of glycerol feedstock may be treated with an anti-polymerizing agent selected from benzoquinone, hydroquinone, methyl hydroquinone, 5-hydroxy-tempo, phenothiazine, or metallic copper. The heteropolyacid catalyst may be selected from silicotungstic acid, phosphotungstic acid, or phosphomolybdic acid. The at least one injection pump may comprise an electric positive displacement pump, wherein the electric positive displacement pump injects the liquid acrolein via pressure conduit, wherein the pressure conduit comprises an in-line pressure sensor downstream of the electric positive displacement pump, and wherein the electric positive displacement pump is interrupted by the pressure sensor upon sensing a predetermined pressure level. The system may further comprise an air-liquid heat exchanger. The system may further comprise a water supply downstream of the air-liquid heat exchanger, wherein the water supply commingles with the acrolein and dilutes the acrolein to a mixture of less than 2%, and wherein the water may be fresh, brackish or filtered produced water combined with the water supply by means of an eductor device or a positive or centrifugal water pump. The system may further comprise a purging container comprising a diluted alkaline solution, wherein the alkaline solution is fed through the pump, reaction chamber, and heat exchanger to denature any residual acrolein. The diluted alkaline solution may be sodium hydroxide, potassium hydroxide, sodium carbonate, or calcium oxide.

In another embodiment of the invention, the system may comprise a feedstock container comprising a mixture of non-aqueous glycerol and at least one heteropolyacid catalyst, at least one injection pump to pull the mixture from the feedstock container through a conduit, a tubular reaction chamber in liquid communication with the conduit and receiving the mixture via the injection pump, wherein the tubular reaction chamber comprises a wall, wherein the tubular reaction chamber is immersed in a heat transfer liquid held in a vessel, and wherein the heat transfer liquid heats the wall of the tubular reactor and the mixture to a temperature sufficient to cause at least one heteropolyacid catalyst to dehydrate the glycerol into acrolein, and insufficient to vaporize the glycerol or acrolein, a liquid-liquid heat exchanger in communication with the tubular reaction chamber which receives and cools the mixture to a lower temperature of less than 150° C., and an air-liquid exchanger in communication with the liquid-liquid heat exchanger which receives and cools the mixture to a lower temperature of less than 38° C. The reaction temperature may be maintained between 250° and 300° C. and pressurized at less than 100 psi. Optionally, the liquid-liquid heat exchanger may be in communication with the mixture prior to the entering the tubular reaction chamber as well as after exiting the tubular reaction chamber, wherein the mixture entering the tubular reaction chamber exchanges its cooler temperature with the higher temperature of the mixture exiting the tubular reaction chamber.

BRIEF DESCRIPTION OF THE DRAWINGS

In the detailed description of various embodiments usable within the scope of the present disclosure, presented below, reference is made to the accompanying drawings, in which.

DETAILED DESCRIPTION OF THE EMBODIMENTS

Before describing selected embodiments of the present disclosure in detail, it is to be understood that the present invention is not limited to the embodiments described herein. The disclosure and description herein is illustrative and explanatory of one or more presently preferred embodiments and variations thereof, and it will be appreciated by those skilled in the art that various changes in the design, organization, order of operation, means of operation, equipment structures and location, methodology, and use of mechanical equivalents may be made without departing from the spirit of the invention.

As well, it should be understood the drawings are intended to illustrate and plainly disclose presently preferred embodiments to one of skill in the art, but are not intended to be manufacturing level drawings or renditions of final products and may include simplified conceptual views as desired for easier and quicker understanding or explanation. As well, the relative size and arrangement of the components may differ from that shown and still operate within the spirit of the invention.

Moreover, it will be understood that various directions such as "upper," "lower," "bottom," "top," "left," "right," and so forth are made only with respect to explanation in conjunction with the drawings, and that the components may be oriented differently, for instance, during transportation and manufacturing as well as operation. Because many varying and different embodiments may be made within the scope of the concept(s) herein taught, and because many modifications may be made in the embodiments described herein, it is to be understood that the details herein are to be interpreted as illustrative and non-limiting.

The present invention relates, generally, to the production of acrolein, by reacting glycerol in a transportable, heated tubular reactor system in the presence of heteropolyacid catalysts, such as silicotungstic acid, phosphotungstic acid, or phosphomolybdic acid, to apply in a continuous injection or batch injection in order to remove iron sulfide and hydrogen sulfide from oil and gas production systems, wastewater injection water systems, enhanced oil recovery water flood systems, produced fluid flow lines, and industrial process water systems.

This invention overcomes the inadequacies of processes based upon a heterogenous packed bed acid catalyst to produce acrolein. The homogenous catalyst can be chosen from a group of heteropolyacids, including silicotungstic acid ($H_4SiW_{12}O_{40} \cdot 15H_2O$, HSiW), phosphotungstic acid ($H_3PW_{12}O_{40} \cdot 14H_2O$, HPW) and phosphomolybdic acid ($H_3PMo_{12}O_{40} \cdot 28H_2O$, HPMo). Heteropolyacids are a class of acids made up of a combination of hydrogen and oxygen, with certain metals and non-metals, such as tungsten, molybdenum or vanadium. This type of acid is a common re-usable acid catalyst in chemical reactions.

The glycerol reactor apparatus in this invention may have various physical embodiments, such as cylindrical or rectangular blocks, each containing passageways capable of flowing glycerol and catalyst through passageways, where heat is transferred to the liquid flow. In one embodiment, the acrolein generating apparatus capable of serving as the glycerol dehydration reactor can be a cylindrical liquid-containing vessel that can be wrapped with an insulating heating jacket apparatus and equipped with a stirring mechanism to circulate the glycerol and heteropolyacid catalysts within the cylindrical liquid-containing vessel. Still another apparatus capable of serving as the glycerol dehydration reactor can be a tubular reactor in either a coil configuration or a non-coil, straight tube, configuration that can be placed within a pressure or non-pressure vessel filled with a heat transfer fluid to heat the pre-catalyzed glycerol flowing inside the tubular coil up to a sufficiently high reaction temperature.

In an embodiment of the present invention, after all or a portion of the glycerol is dehydrated and converted to acrolein in the reactor, and upon exiting the heated tubular reactor, the crude acrolein liquid is directed into a liquid-liquid heat exchanger where it exchanges the high heat with the inlet feed pre-catalyzed glycerol, pre-heating the pre-catalyzed glycerol upstream of the heated tubular reactor. The crude acrolein leaving the liquid-liquid heat exchanger is directed into a liquid-air heat exchanger which serves to lower the temperature of the crude acrolein liquid product sufficiently, down to less than 50° C., prior to the injection into a fluid system. The liquid displacement of the acrolein product from within the reactor vessel is managed by injecting a fluid or gas to displace the fluid within the reactor vessel injecting the crude acrolein into a flowing stream of water of sufficient flowing volume so the active acrolein concentration within the water stream is less than 2% by volume. It can be advantageous to cool the acrolein product quickly to minimize the formation of by-products.

In another embodiment of the present invention, the pre-catalyzed glycerol is pumped by means of a positive displacement or other type of pump continuously into a tubular coil or non-coil, straight tube reactor which is placed within a pressurized or non-pressurized vessel containing a heat transfer liquid. The liquid heat transfer liquid is heated by means of an electric resistance heater or by a gas-fired or oil-fired heater up to a constant reaction temperature of 250° C. to 280° C. As the pre-catalyzed glycerol flows into the tubular reactor it reaches reaction temperature and undergoes the dehydration of the glycerol into crude acrolein product. The tubular reactor is sufficiently sized to allow for the increase in the temperature of the inlet pre-catalyzed glycerol and maintain reaction temperature for a period of at least 20 to 40 minutes. In a preferred embodiment, the heat transfer fluid is heated by immersing an electrical resistance heater into the heat transfer fluid vessel or by immersing a steam coil heat exchanger into the heat transfer fluid vessel. The total liquid residence time for the pre-catalyzed glycerol within the tubular reactor coil or tubular reactor is directly controlled by the volumetric flow rate of feed injection. The liquid-holding capacity of the tubular reactor is sized sufficiently to allow for a given acrolein volume output and manage the liquid residence time within the tubular coil or non-coil, straight tube reactor to achieve sufficient catalytic dehydration and conversion of glycerol into acrolein product. An embodiment of the present invention avoids the production of acrolein vapors upstream of the point of injection. The pressure pump utilized in an embodiment of the reactor where it is in contact with only the pre-catalyzed glycerol feed not the resultant acrolein product. The tubular reactor and the downstream conduit and heat exchangers provide a closed system for the crude acrolein product to travel through before entering the fluid system being treated.

In another embodiment of the present invention, the pre-catalyzed glycerol is pumped by means of a positive displacement or other type of pump continuously into a tubular coil or non-coil, straight tube reactor placed within a pressurized or non-pressurized vessel containing a heat transfer liquid. The liquid heat transfer liquid is heated by means of an electric resistance heater or by a gas-fired or oil-fired heater up to a constant reaction temperature of 250° C. to 280° C. As the pre-catalyzed glycerol flows into the tubular reactor it reaches reaction temperature and undergoes the dehydration of the glycerol into crude acrolein product. The tubular reactor is sufficiently sized to allow for the increase in the temperature of the inlet pre-catalyzed glycerol and maintain reaction temperature for a period of at least 20 to 40 minutes.

In an embodiment, the heat transfer fluid is heated by immersing an electrical resistance heater into the heat transfer fluid vessel or by immersing a steam coil heat exchanger into the heat transfer fluid vessel. The total liquid residence time for the pre-catalyzed glycerol within the tubular reactor coil or tubular reactor can be directly controlled by the volumetric flow rate of feed injection. The liquid-holding capacity of the tubular reactor is sized sufficiently to allow for a given acrolein volume output and to manage the liquid residence time within the tubular coil or non-coil, straight tube reactor to achieve sufficient catalytic dehydration and conversion of glycerol into acrolein product. A method embodiment of the present invention avoids the production of acrolein vapors upstream of the point of injection. The pressure pump utilized in an embodiment of the present invention can be located upstream of the reactor where it is in contact with only the pre-catalyzed glycerol feed not the resultant acrolein product. The tubular reactor and the downstream conduit and heat exchangers provide a closed system for the crude acrolein product to travel through before entering the fluid system being treated.

In applications requiring higher pressures (greater than 340 kPa [or 50 psi]) a second positive displacement chemical injection pump can be positioned downstream of the acrolein product air/liquid heat exchanger. A small stainless-steel reservoir holding approximately 1 quart of fluid can be installed in the conduit line to provide a pump suction buffer fluid volume to aid in the high pressure positive displacement injection pump efficiency. In an embodiment, the production of acrolein, via glycerol dehydration, is performed in a thermo-catalytic process in the liquid phase inside a tubular reactor.

Figure 1:
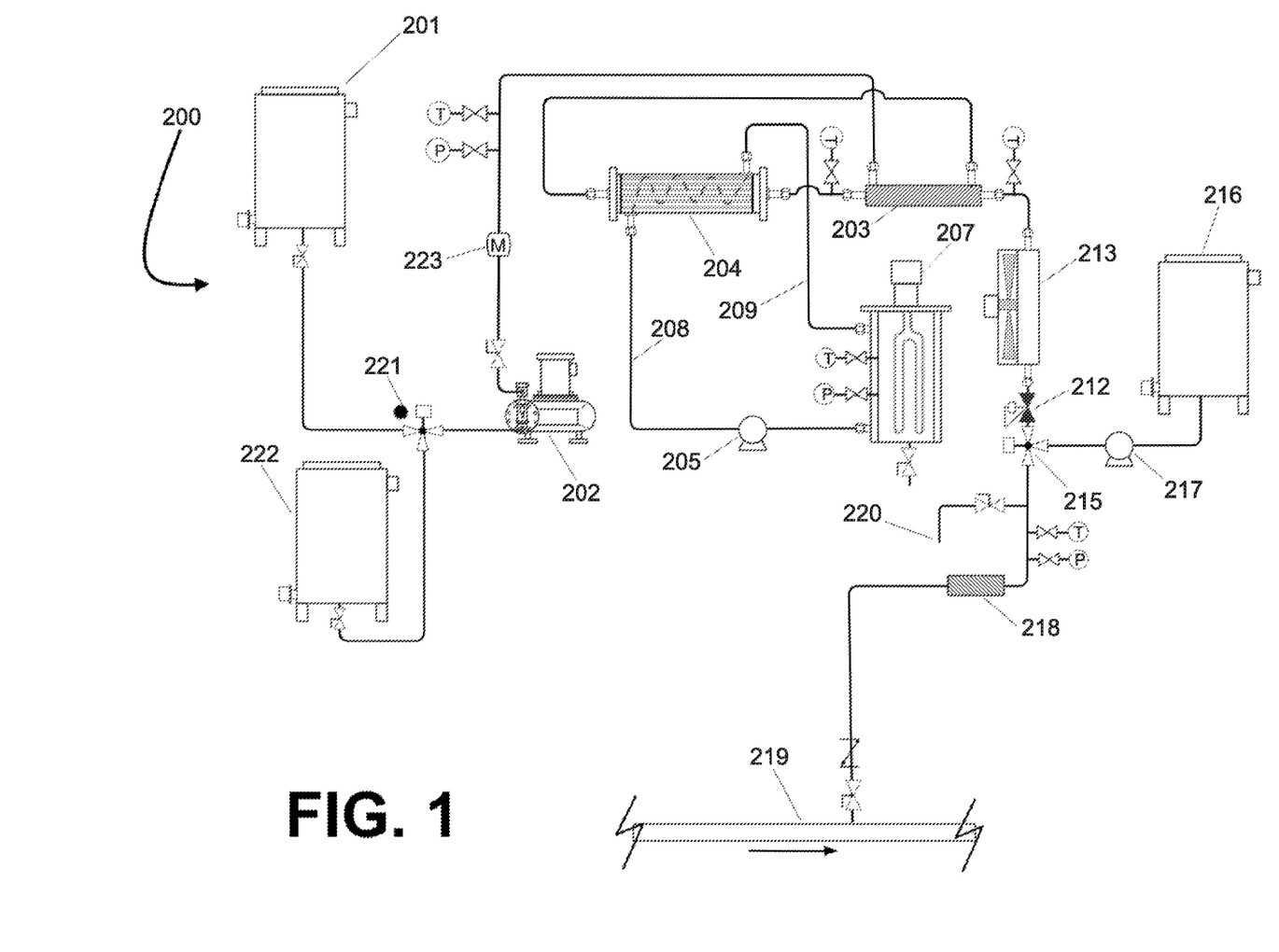
FIG. 1 depicts a diagram of an embodiment of a tubular reactor system usable in the present invention.

Turning now to FIG. 1, a diagram of the tubular reactor design 200 is shown. Feedstock container 201 is a portable container in which the glycerol can be pre-combined with the preferred catalyst and other functional additives. Then, the pre-catalyzed glycerol blend can be pumped from feedstock container 201 with, for example, a positive displacement pump 202 into a tubular liquid—liquid heat exchanger 203, which can be used to lower the temperature of the liquid exiting the tubular reaction and raise the temperature of the pre-catalyzed glycerol feedstock upstream of entering into the acrolein tubular reactor 204. The tubular reactor 204 is housed within a chamber filled to approximately 95% capacity with heat transfer oil which is held within the heat transfer fluid container and heated by means of an electric resistance heater immersed in the heat transfer fluid, and/or the heat transfer fluid may be circulated via conduits 208 and 209 to and from a heat transfer fluid heating system 207 to temperatures up to 300° C. for providing sufficient heating to the tubular reactor. The heat transfer fluid flows into the reactor vessel through a heat transfer fluid conduit. The heat transfer fluid is pumped with a heat transfer fluid pump 205. The heat transfer fluid pump 205 is powered by an electric motor which is controlled by the systems electronic controller and can be adjusted to allow for different heat transfer fluid flow rates to manage the heat transfer fluid temperature in the reactor vessel. The glycerol feedstock storage tank is heated with a heating device and the level of the glycerol in the tank is measured by a liquid level sensor.

The reaction tube conduits inside of the reactor vessel 204 can be fabricated from multiple parallel straight tube conduits in a typical tube and shell arrangement. The feed glycerol enters the reactor vessel through a fluid passage port at one end and exits the reactor vessel through a fluid passage port at the opposite end. Once the glycerol feed enters the reactor vessel through the inlet fluid passage port, it is distributed to two or more tubing conduits that are fixed in a tube sheets. Tube sheets are plates drilled to provide holes through which reactor tube conduits are placed. There is a tube sheet located on each end of the reactor vessel. The tube sheet is made of a round flat steel plate with holes drilled to accept the reactor tubes or pipes in an accurate location and pattern to one another. The tubes are inserted through the holes in the tube sheet and held firmly by welding, mechanical or hydraulic expansion. The tube sheet is welded or bolted to the interior surface of the reactor vessel. The tube sheet is used to support, isolate, and prevent the reaction fluid on the tube side from mixing with the heat transfer fluid on the shell side. There is a tube sheet on each end of the reactor vessel to support and isolate the reactor tubes or pipes. The vessel and tube arrangement form a typical tube and shell heat exchanger design where the heat transfer fluid is external to the tube and the glycerol reactant is internal within the tube. The tube size and length are identical to each other. The length of the tube bundles may vary and are designed based upon the desired throughput production volume of the reactor for production of acrolein containing fluid. Baffles can be positioned within the tube bundle section to aid in the heat transfer fluid flow in a more efficient manner. Baffles are flow directing and obstructing vanes in typical shell and tube exchangers and are an integral part of the heat transfer fluid design. The baffles serve to support the tubes, maintain separation of the tubes, and direct the flow of the heat transfer fluid through the reactor tube bundle.

The pressure inside the tubular reactor reaction conduit can be controlled using an inline back-pressure regulator valve 212 positioned in the conduit downstream of the acrolein product heat exchanger 213, and can be maintained between 100 kPa (10 psi) and 1380 kPa (200 psi). The acrolein air-liquid heat exchanger 213 reduces the temperature of the dilute glycerol/acrolein solution to below 95° C., preferably less than 35° C. One preferred method of application includes blending the acrolein product with dilution water from a water source available at the location either in storage, from a water well, or from produced water piped from oil well oil/water separator. The water, from water source 216, can be injected into the acrolein product stream using a positive displacement pump 217 at mixing valve 215, with the dilute acrolein solution. The blend of acrolein product with water can be further blended through an in-line static mixing device 218. The volume of water blended into the acrolein product solution will depend upon the volume of acrolein required for treatment. A process sample of the acrolein product can be manually obtained from a sample point 220.

If process conditions or operator preference requires shut down of the operating process, a formal shut down procedure discontinues glycerol feed and diverts using a three-way valve 221 to draw a displacement fluid stored in nearby bulk tank 222.

The flow of glycerol from the storage tank into the tubular reactor is metered by a positive displacement fluid meter 223 with the output information captured by an electronic process controller or electronic data logging device (not shown).

In still another method of use, the acrolein product can be injected at a low injection rate directly into the system to be treated at levels determined by the concentration of sulfides within the water system.

When acrolein is finally injected into the flowline or other area of the oil well process 219 system to dissolve iron sulfide or scavenge hydrogen sulfide, the concentration should be less than 1.5% by volume within the stream of fluids at the point of injection to avoid any potential for downstream polymerization of acrolein to occur.

The system may comprise a liquid acrolein neutralizing solution made up of a dilute alkaline solution (including, but not limited to, sodium hydroxide, potassium hydroxide, calcium oxide, sodium carbonate, or combinations thereof) stored in bulk tank 222 and fed into chemical injection pump conduit by valve 221. The acrolein neutralizing solution reduces the toxic character of any residual acrolein in the system.

Figure 2:
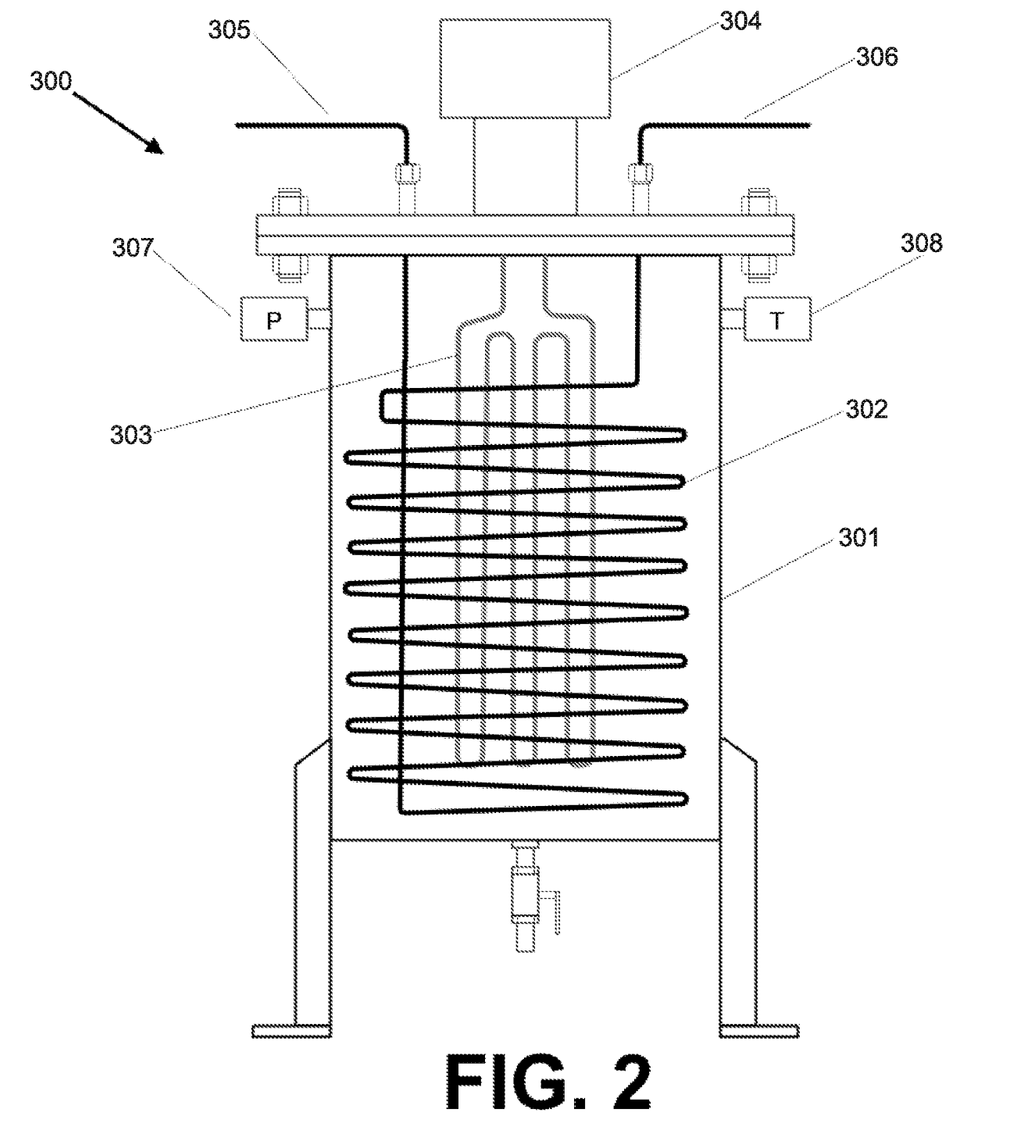
FIG. 2 depicts a diagram of an embodiment of a coiled tubular reactor, an alternative embodiment to the tubular reactor depicted in FIG. 1.

Referring to FIG. 2, an alternative coiled tubing reactor design 300 is depicted. As depicted in FIG. 1, the reactor vessel and reactor tubing conduit within the reactor vessel is a straight tube or conduit reactor design. The coil tube reactor depicted in FIG. 2 can be interchanged for the straight tube reactor. In the alternative reactor design, a low-pressure vessel 301 constructed of steel material suitable for high temperatures of up to 350° C., serves as the reactor vessel. The reactor vessel is a container utilized to house the tubing coil conduit 302 and the internal electrical resistance heating element 303. The electrical resistance heating element can be controlled by an attached electrical controller 304 located external to the reactor vessel and mounted onto the enclosure cover plate of the reactor. The reactor vessel is filled to within 4 to 5 inches from the top of the vessel with a heat transfer oil fluid which can be capable of a working temperature of up to 315° C., serving to transfer the heat created by the electrical resistance heating coil immersed in the heat transfer fluid over to the reactor tubing coil conduit containing the glycerol and/or glycerol acrolein product. The reactor coil tubing conduit can receive glycerol feed via a fluid passage port 305, which can travel from within the reactor vessel through the top flange enclosure of the reactor vessel, as shown. During the process, the glycerol feed flows downward through the coil conduit, and exits the reactor vessel via fluid passage port 306, which flows from within the reactor through the port in the reactor vessel top flange enclosure. The pressure within the reactor vessel can be continuously monitored by an electronic pressure transmitter 307 affixed onto the body of the reactor vessel, or alternatively mounted on the top flange enclosure, and can be maintained at less than 690 kPa (100 psi). The temperature of the heat transfer fluid inside the reactor vessel can be continuously monitored by an electronic pressure transmitter 308, which can be affixed onto the body of the reactor vessel, or alternatively mounted on the top flange enclosure. Additionally, a layer of insulating material, completely lining the exterior surface of the vessel and allowing for access of fluid ports and monitoring devices, is used to reduce heat loss of the heat transfer fluid within the vessel.

The reactor vessel depicted in FIGS. 1 and 2 can, alternatively, be heated by an external electrical resistance heating element or by an externally attached hot oil jacket.

Figure 3:
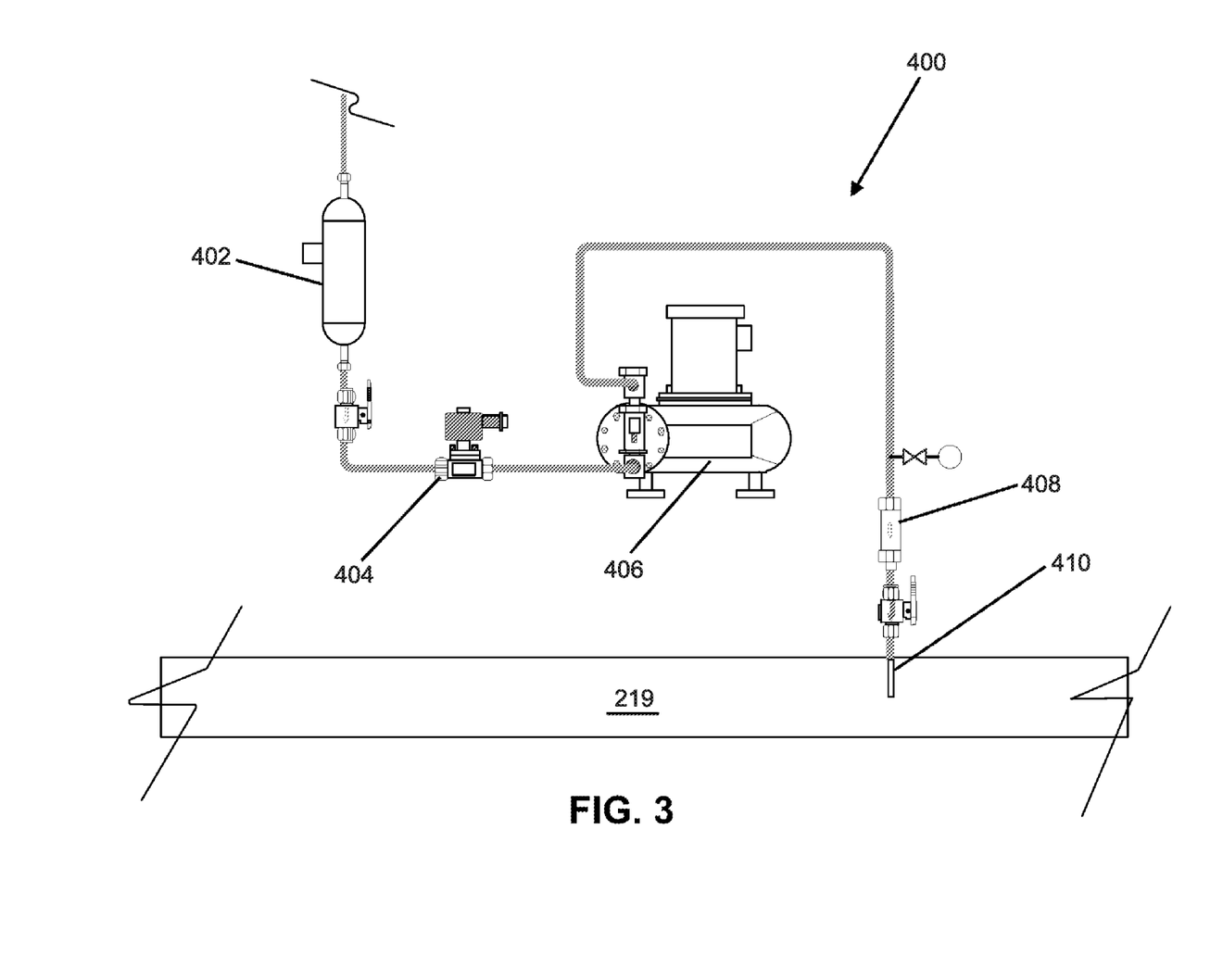
FIG. 3 depicts a diagram of an embodiment of a supplemental pressure injector which may be used with the tubular reactor system depicted in FIG. 1.

Turning now to FIG. 3, the reactor vessel depicted in FIGS. 1 and 2 can alternatively include a high-pressure injection system 400 located downstream of the glycerol/acrolein product heat exchangers. High-pressure injection system 400 comprises a pump suction vessel 402 receiving the reactor product downstream from static mixer 218 (depicted in FIG. 1). A solenoid valve 404 can be used to meter the reactor product as it flows into a high pressure pump 406. Product can be injected into water flow line 219 by means of an injection quill 410; back pressure can be prevented by use of a check valve 408. High-pressure injection system 400 allows continuous or intermittent fluid injection of the acrolein-containing fluid into a fluid system at system pressures greater than 340 kPa (50 psi).

Figure 4:
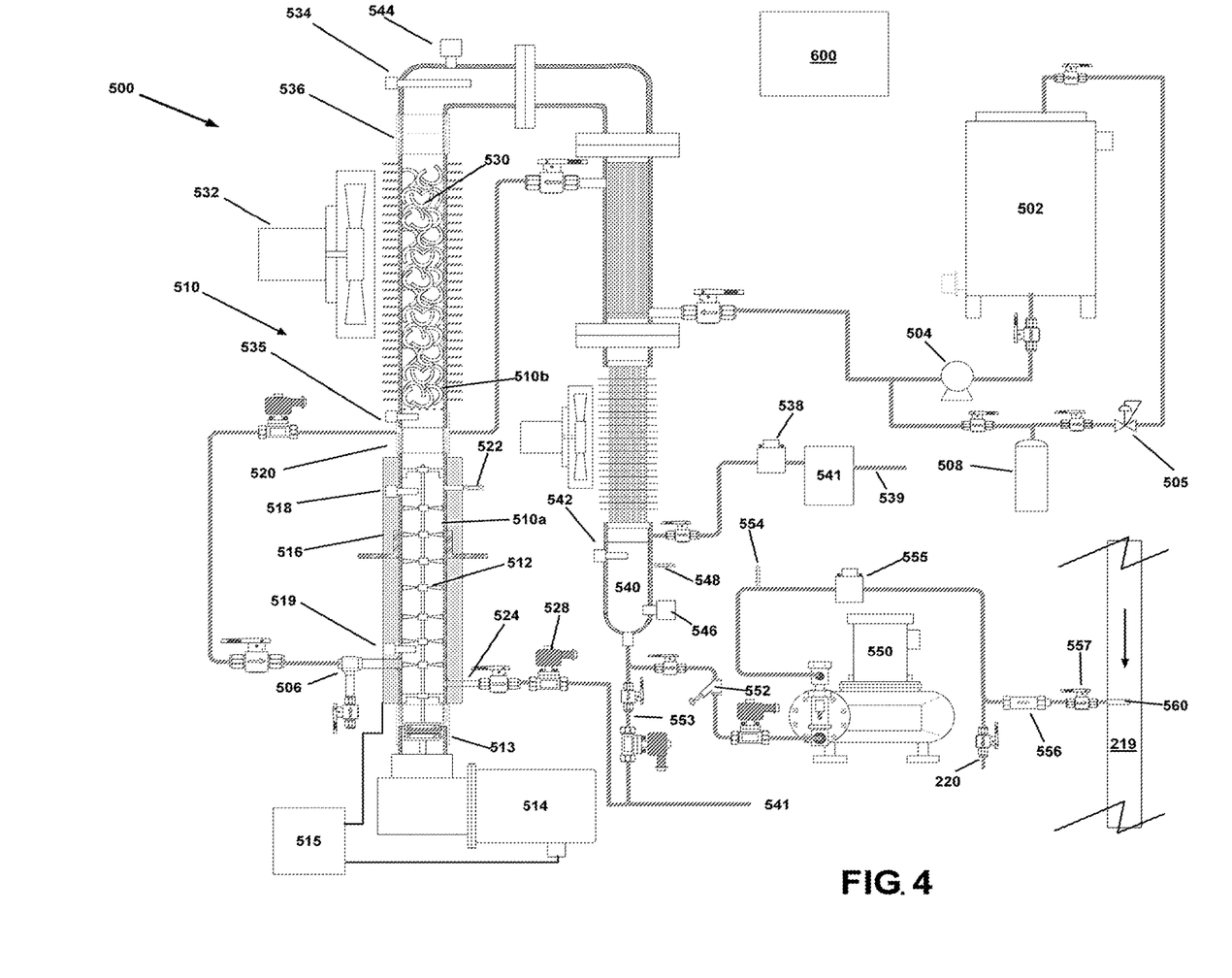
FIG. 4 depicts a diagram of an in-line mixer embodiment of the tubular reactor system.

Turning now to FIG. 4, an alternative embodiment of the design 500 is shown. The glycerol containing catalyst and other functional materials enter under low pressure from a feed tank 502, and flows into the lower section 510a of the inline stirred reactor vessel 510 via a feed inlet 506 fed by a feed pump 504. The glycerol feed tank 502 can be connected to a nitrogen gas source 508 via a conduit. The nitrogen serves to prevent oxygen in air from entering the tank as the glycerol feed is pumped into the reactor system. The nitrogen pressure can be controlled with a pressure regulator 505 in the conduit leading to the glycerol feed tank 502. The nitrogen can also be connected to the conduit feeding the glycerol into the inline stirred reactor 510. Upon startup, the entire system 500 is purged with nitrogen to void the system of air before starting the system and filling the reactor with glycerol. System controller 600 is not depicted in FIG. 4 with any lines extended from it for clarity, and also because system controller 600 may utilize wired or wireless data transmission (e.g., wi-fi, Bluetooth) to receive input from all temperature, pressure, and liquid level sensors described herein.

The inline stirred reactor 510 can be equipped with an internal stirring apparatus 512. The internal stirring apparatus 512 can be actuated by an electric motor 514 that can be powered by power source 515 and coupled to stirring apparatus 512, with a magnetic drive coupling 513 to stir the glycerol feed in the reactor 510. The reactor 510 can be heated by an external heating jacket 516.

The heating jacket 516 may be heated by either an electric resistance heating element, which can be wrapped in an insulating medium, or a liquid heat transfer fluid in an external heating jacket. The electric heating jacket 516 temperature can be controlled by either a thermostat integral to the electric heating jacket or by the system controller 600 monitoring the temperature. The stirring of the glycerol feed within the reactor aids in maintaining a homogenous fluid mix and provides for thorough and consistent heating throughout the liquid in the reactor. The temperature of the liquid within the reactor can be monitored with thermocouples 518 and 519. The proper liquid level can be monitored by a level controller 520 that can be connected to system controller 600 which controls the feed pump 504 rate. The pressure inside the inline stirred reactor can be measured and monitored by a level pressure sensor 522 connected to system controller 600. The inline stirred reactor can be fitted with an outlet 524 at the base of the reactor 510 with said outlet 524 connected to a conduit connected to a vapor scrubber 541 (duplicated in FIG. 4 for convenience) to hold the blow down of liquids from within the reactor. The blow down can be controlled by a motor valve 528 connected to the system controller 600 which directs the motor valve 528 to open and release fluids. The blow down of liquids from within the reactor 510 is intended to lower the catalyst concentration from glycerol.

As shown, upper section 510b of the inline stirred reactor 510 comprises a reflux column 530. The reflux column serves to control the condensation of heavy condensable vapors, such as the glycerol in the reactor. The air fan 532 blows across the reflux column 530 which serves to lower the temperature of the gases rising from the higher temperature in the stirred reactor 510. The temperature across the reflux section is measured by thermocouples 534 and 535 which are monitored by the system controller 600. By maintaining the proper outlet temperature, the lighter condensable vapors, such as the water and acrolein, exit the top outlet 536 of the reactor 510. The reflux column 530 is typically filled with an inert ceramic or stainless-steel packing which aids in vapor distribution as well as providing greater liquid surface area within the column. The pressure of the reflux accumulator 540 and the inline stirred reactor 510 can be maintained by a back-pressure regulator valve 538, which can be located in the non-condensable vapor line, releasing non-condensable vapor from the reflux accumulator 540 and the vapor scrubber 541. Vapor scrubber 541 leads to a vent 539.

The light condensable vapors leaving the reflux section are directed, via a conduit, into an air or liquid heat exchanger to reduce the temperature below the boiling point of acrolein 53° C. (127° F.). This results in the acrolein and other light condensable vapors with boiling points at or below this temperature to enter the reflux accumulator 540. The liquid level in the reflux accumulator is monitored by a level sensor 542, which reports to the system controller 600. This level control is used to control the pump rate of the injection pump 550. The pressure of the gas above the liquid level is monitored by pressure gauge 544, which reports pressure to system controller 600. The temperature and pressure of the liquid in the reflux accumulator can be monitored with a thermocouple 546 and pressure sensor 548 and reported to the system controller 600.

The condensed liquid can be directed to the injection pump 550, via a conduit, which first passes through an inline filter 552 to remove any unwanted particulates. A drain line 553 can be located in the conduit line upstream of the chemical injection pump. The chemical injection pump 550 can be a positive displacement pump connected via conduit to the water flow line 219. The discharge pressure of the chemical injection pump 550 can be monitored with a pressure sensor 554 which sends pressure information to the system controller 600. A positive displacement chemical meter 555 can be located downstream of the chemical injection pump 550. The injection conduit immediately upstream of the injection point can be equipped with a double check valve 556 to prevent fluids from the water flow line from traveling up conduit to the chemical injection pump 550. A manual valve 557 can be connected directly downstream of the check valve and on the water flow line. A chemical injection quill 560 can penetrate the interior cross section of the water flow line 219 to release the chemical in the center of the water flow to aid in dispersion. Sample point 220 fulfills the same purpose as in the embodiment of FIG. 1.

At various points in the system, temperature sensors are used to monitor the temperature of the flow of glycerol feed and reactants to ensure the reaction is taking place at design temperatures. Temperature above 300° C. are unnecessary and may present a risk of over-pressurizing the system, while temperatures in the 250° C. to 270° C. range result in more efficient reactions and production of acrolein. The electronic process control system tracks and monitors the temperature of all temperature measurement devices. The temperature data collected can be reported locally on a control panel and transmitted to remote monitoring via a cellular and/or satellite transmission device. At various points in the reactor system, high temperature and high-pressure shutdown controls will prevent temperatures and pressures from exceeding the design values of the equipment and components.

The air-liquid heat exchanger located downstream of the tubular reactor uses either a tubular coil or straight tubes, optionally fitted with heat exchanger fins on the body of the straight tubing conduit or coil tubing conduit. Optionally, the cooling air is blown via an electric blower fan and directed up through and around the air-liquid heat exchanger and exhausted out of the process enclosure through an air exhaust port. As the air is blown into the air exchanger it passes through an activated carbon bed which filters the air drawn by the blower from within the system enclosure. The purpose of the activated carbon is to adsorb volatile carbon compounds present in the air before exhausting into the atmosphere.

While various embodiments usable within the scope of the present disclosure have been described with emphasis, it should be understood that within the scope of the appended claims, the present invention can be practiced other than as specifically described herein.

The invention claimed is:

1. A system of continuous production and injection of acrolein for the treatment of sulfides, the system comprising:
   a feedstock container holding a fluid comprising non-aqueous glycerol;
   a fluid pressure pump carrying the fluid from the feedstock container through a conduit;
   a vessel comprising a heat transfer liquid and an electric resistance heater, steam coil, gas-fired heater, oil-fired heater, or combination thereof immersed in the heat transfer liquid; and
   a tubular reaction chamber within the vessel in liquid communication with the conduit, wherein the tubular reaction chamber is heated to bring the fluid to a temperature sufficient to activate at least one heteropolyacid catalyst mixed with the non-aqueous glycerol, wherein the at least one heteropolyacid catalyst dehydrates the glycerol into acrolein.

2. The system of claim 1, wherein the fluid enters a liquid-liquid heat exchanger between the feedstock container and the tubular reaction chamber.

3. The system of claim 1, wherein the heteropolyacid catalyst is mixed with the fluid upstream from the tubular reaction chamber.

4. The system of claim 1 wherein the heat transfer liquid is heated to room temperature.

5. The system of claim 1, wherein the tubular reaction chamber comprises a coiled conduit of sufficient capacity to hold the fluid within the tubular reaction chamber until the dehydration is completed.

6. The system of claim 5, wherein the fluid is retained within the tubular reaction chamber for at least 30 minutes at between 250° C. and 300° C.

7. The system of claim 1, wherein the reaction chamber is heated by electrical resistance heat, indirect gaseous fuel heat, the heat transfer liquid, or combinations thereof.

8. The system of claim 1, wherein the pressure of the tubular reaction chamber is maintained between 100 kPa and 1380 kPa.

9. The system of claim 1, wherein the glycerol in the feedstock container is treated with an anti-polymerizing agent selected from one or more of the group comprising: benzoquinone, hydroquinone, methyl hydroquinone, 5-hydroxy-tempo, phenothiazine, and metallic copper.

10. The system of claim 1, wherein the at least one heteropolyacid catalyst is selected from one or more of the group comprising: silicotungstic acid, phosphotungstic acid, and phosphomolybdic acid.

11. The system of claim 1, wherein the at least one injection pump comprises an electric positive displacement pump, wherein the electric positive displacement pump injects the liquid acrolein via pressure conduit, wherein the pressure conduit comprises an in-line pressure sensor downstream of the electric positive displacement pump, and wherein the electric positive displacement pump is interrupted by the pressure sensor upon sensing a predetermined pressure level.

12. The system of claim 1, further comprising an air-liquid heat exchanger downstream from the tubular reaction chamber.

13. The system of claim 12, further comprising a water supply of fresh, brackish, or filtered produced water downstream of the air-liquid heat exchanger, wherein the water supply commingles with the acrolein and dilutes the acrolein to a mixture of less than 2%.

14. The system of claim 13, wherein the acrolein is combined with the water supply by means of a positive or a centrifugal water pump.

15. The system of claim 1, further comprising a purging container comprising a diluted alkaline solution, wherein the alkaline solution is fed through the fluid pressure pump and the tubular reaction chamber to denature any residual acrolein.

16. The system of claim 15, wherein the diluted alkaline solution is selected from one or more of the group comprising: sodium hydroxide, potassium hydroxide, sodium carbonate, and calcium oxide.

17. A system of continuous production and injection of acrolein containing fluid for the treatment of sulfides, the system comprising:
   a feedstock container comprising a non-aqueous glycerol;
   at least one injection pump to pull the non-aqueous glycerol from the feedstock container through a conduit;
   a tubular reaction chamber in liquid communication with the conduit and receiving the non-aqueous glycerol via the at least one injection pump, wherein the tubular reaction chamber comprises a wall, wherein the tubular reaction chamber is immersed in a heat transfer liquid held in a vessel, and wherein the heat transfer liquid heats the wall of the tubular reactor to a temperature sufficient to cause at least one heteropolyacid catalyst mixed with the non-aqueous glycerol to dehydrate the non-aqueous glycerol into acrolein, and insufficient to vaporize the non-aqueous glycerol or acrolein;
   a liquid-liquid heat exchanger in communication with the tubular reaction chamber which receives and cools the mixture to a temperature of less than 150° C.; and an air-liquid exchanger in communication with the liquid-liquid heat exchanger which receives and cools the mixture to a temperature of less than 38° C.

18. The system of claim 17, wherein the reaction temperature is maintained between 250° and 300° C.

19. The system of claim 17, wherein the liquid-liquid heat exchanger is in communication with the non-aqueous glycerol prior to the mixture entering the tubular reaction chamber as well as after exiting the tubular reaction chamber, wherein the fluid entering the tubular reaction chamber exchanges its cooler temperature with the higher temperature of the fluid exiting the tubular reaction chamber.

20. The system of claim 17, wherein the pressure of the tubular reactor is maintained at less than 690 kPa.

* * * * *